(12) United States Patent
Langkilde

(10) Patent No.: US 7,855,082 B1
(45) Date of Patent: Dec. 21, 2010

(54) RAMAN SPECTROSCOPIC METHOD FOR DETERMINING THE RATIO OF 5-METHOXY AND 6-METHOXY ISOMERS OF OMEPRAZOLE

(75) Inventor: Frans Langkilde, Skodsborg (DK)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/350,665

(22) Filed: Jan. 8, 2009

Related U.S. Application Data

(63) Continuation of application No. 11/284,434, filed on Nov. 21, 2005, now abandoned, which is a continuation of application No. 10/284,828, filed on Oct. 31, 2002, now abandoned.

(60) Provisional application No. 60/334,853, filed on Oct. 31, 2001.

(51) Int. Cl.
*G01N 21/00* (2006.01)

(52) U.S. Cl. ............... 436/164; 436/171; 546/273.7

(58) Field of Classification Search ............ None
See application file for complete search history.

(56) References Cited

U.S. PATENT DOCUMENTS

| | | | |
|---|---|---|---|
| 4,255,431 A | 3/1981 | Junggren et al. |
| 6,150,380 A | 11/2000 | Lövqvist et al. |
| 6,262,085 B1 | 7/2001 | Whittle et al. |
| 6,262,086 B1 | 7/2001 | Whittle et al. |
| 6,268,385 B1 | 7/2001 | Whittle et al. |
| 6,287,594 B1 | 9/2001 | Wilson et al. |
| 6,312,712 B1 | 11/2001 | Whittle et al. |
| 6,312,723 B1 | 11/2001 | Whittle et al. |
| 6,316,020 B1 | 11/2001 | Whittle et al. |
| 6,326,384 B1 | 12/2001 | Whittle et al. |
| 6,365,180 B1 | 4/2002 | Meyer et al. |
| 6,369,087 B1 | 4/2002 | Whittle et al. |
| 6,384,059 B1 | 5/2002 | Lövqvist et al. |
| 6,444,689 B1 | 9/2002 | Whittle et al. |
| 6,608,091 B2 | 8/2003 | Whittle et al. |
| 6,653,329 B1 | 11/2003 | Whittle et al. |
| 6,667,321 B2 | 12/2003 | Whittle et al. |
| 6,667,323 B1 | 12/2003 | Whittle et al. |
| 6,667,324 B1 | 12/2003 | Whittle et al. |
| 6,673,936 B2 | 1/2004 | Whittle et al. |
| 6,706,737 B2 | 3/2004 | Whittle et al. |
| 6,780,880 B1 | 8/2004 | Whittle et al. |
| 2002/0103232 A1 | 8/2002 | Whittle et al. |
| 2002/0156103 A1 | 10/2002 | Whittle et al. |

(Continued)

FOREIGN PATENT DOCUMENTS

WO   WO 01/14367   3/2001

OTHER PUBLICATIONS

Ohishi et al., Acta Cryst (1989), C45, 1921-1923.

(Continued)

*Primary Examiner*—Yelena G Gakh
(74) *Attorney, Agent, or Firm*—White & Case LLP

(57) ABSTRACT

The present invention relates to a novel method to determine the ratio of 5-methoxy and 6-methoxy isomers of omeprazole present in a mixture thereof. The method uses different Raman scattering efficiency values for the 5-methoxy and 6-methoxy isomers. This is of importance since the two isomers have different stability in the solid state in bulk form and in admixture with pharmaceutical excipients.

4 Claims, 6 Drawing Sheets

Correlation of fraction of 5-isomer determined with FT-Raman and ssNMR analysis.

U.S. PATENT DOCUMENTS

| | | |
|---|---|---|
| 2002/0156284 A1 | 10/2002 | Lövqvist et al. |
| 2003/0088106 A1 | 5/2003 | Whittall et al. |
| 2003/0096845 A1 | 5/2003 | Whittle et al. |
| 2003/0225135 A1 | 12/2003 | Whittle et al. |
| 2003/0225136 A1 | 12/2003 | Whittle et al. |
| 2003/0225137 A1 | 12/2003 | Whittle et al. |
| 2004/0157887 A1 | 8/2004 | Whittle et al. |
| 2005/0032842 A1 | 2/2005 | Lövqvist et al. |
| 2005/0176774 A1 | 8/2005 | Whittle et al. |
| 2006/0014799 A1 | 1/2006 | Whittle et al. |

OTHER PUBLICATIONS

Langkilde et al., J. Pharm. Biomed. Anal., 15 (1997), 687-696.
Taylor et al., Pharm. Res., vol. 15, No. 5, 1998, 755-761.

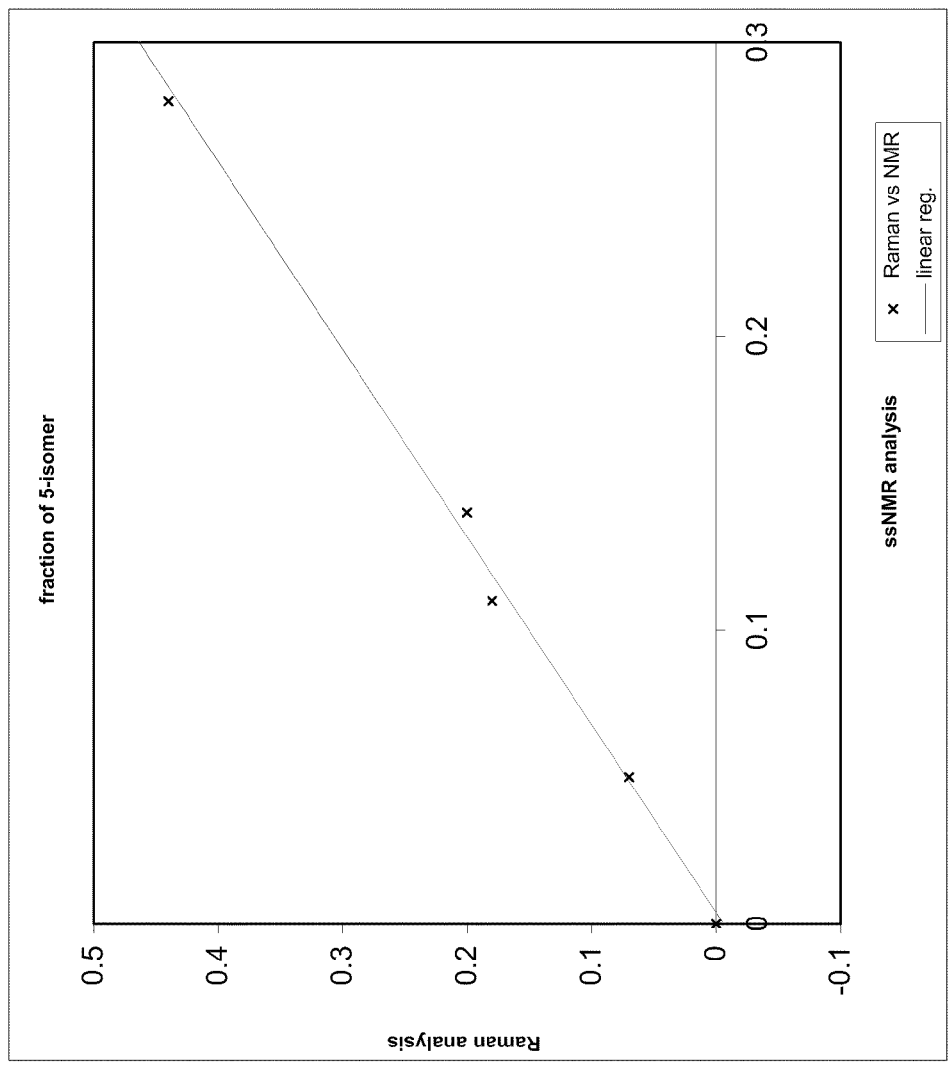
Figure 1. Correlation of fraction of 5-isomer determined with FT-Raman and ssNMR analysis.

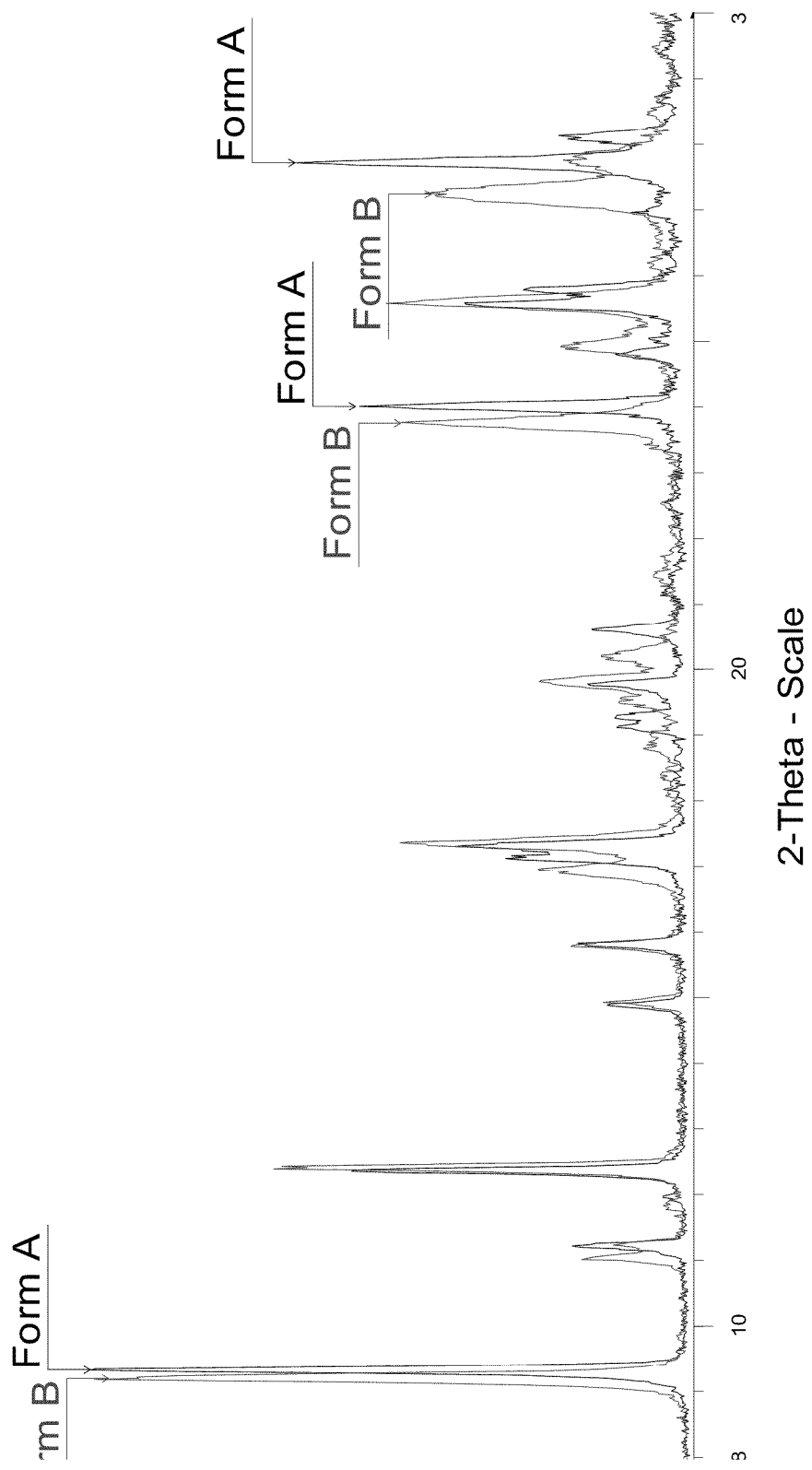
Figure 2. XRPDs of omeprazole form A and form B in the range 2θ 8-30°, showing the different diffractograms.

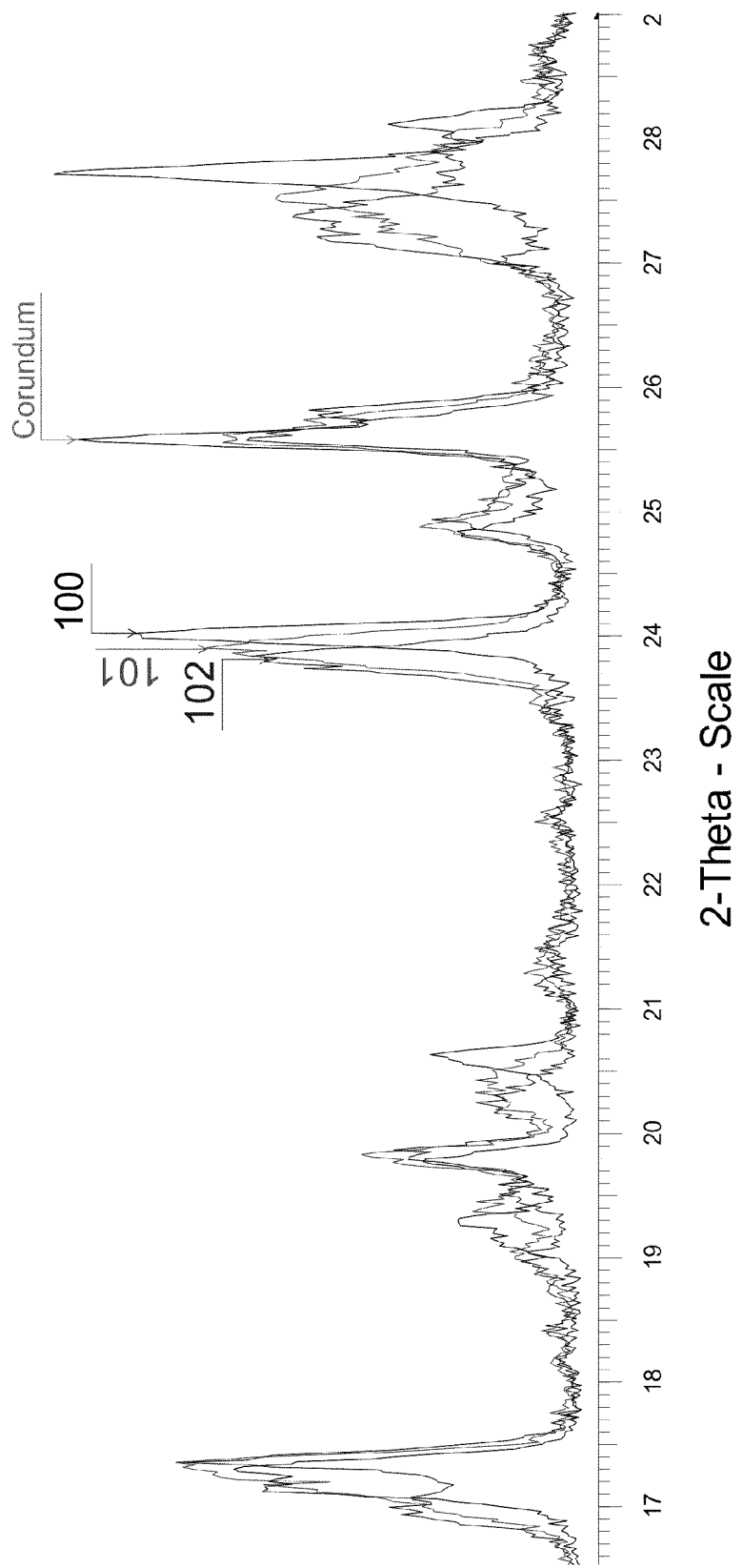
Figure 3. XRDPs of three different batches of omeprazole: 100 (form A); 101 (form A/B); and 102 (form B).

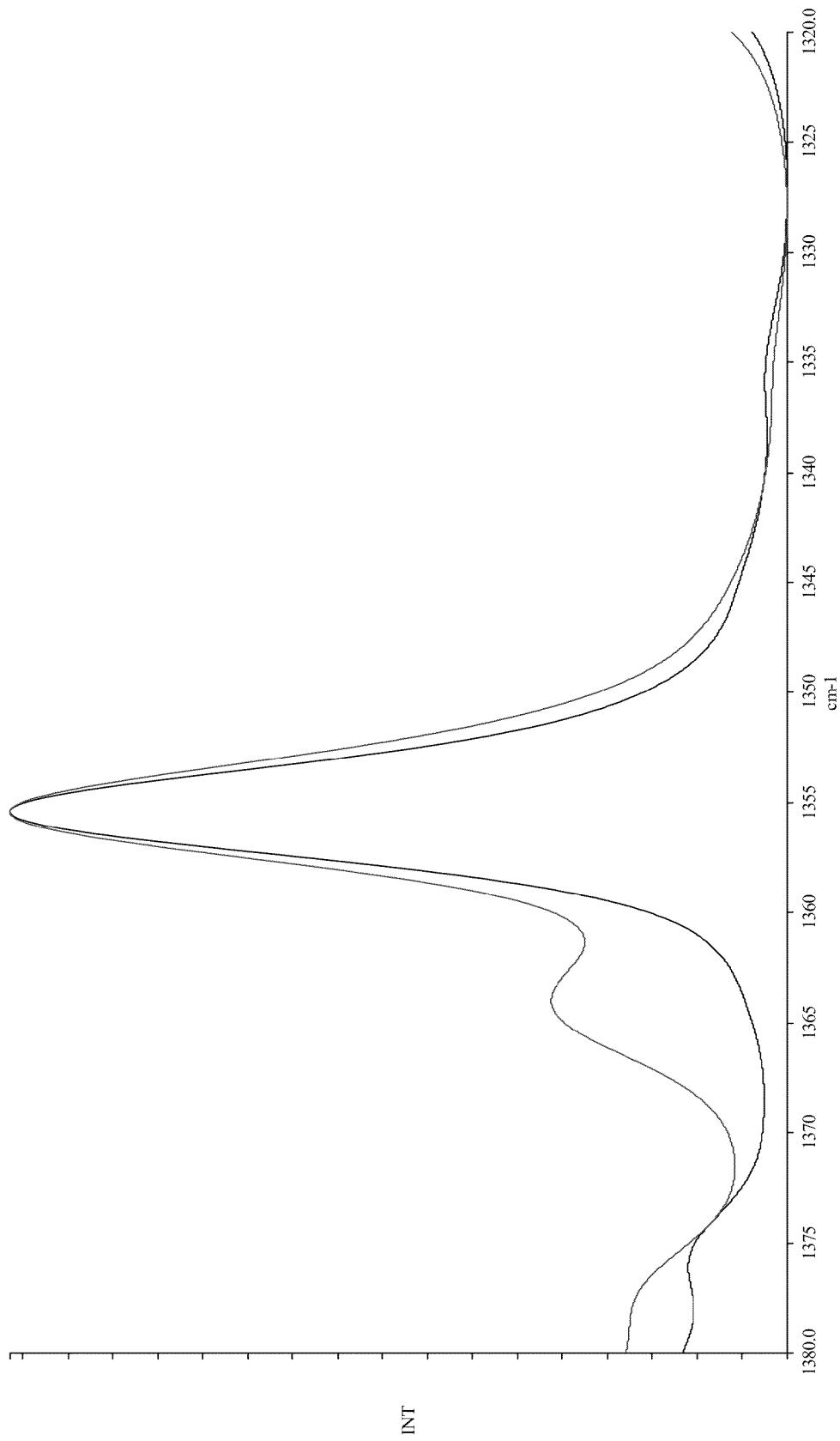
Figure 4. FT-Raman spectra of forms A and B.

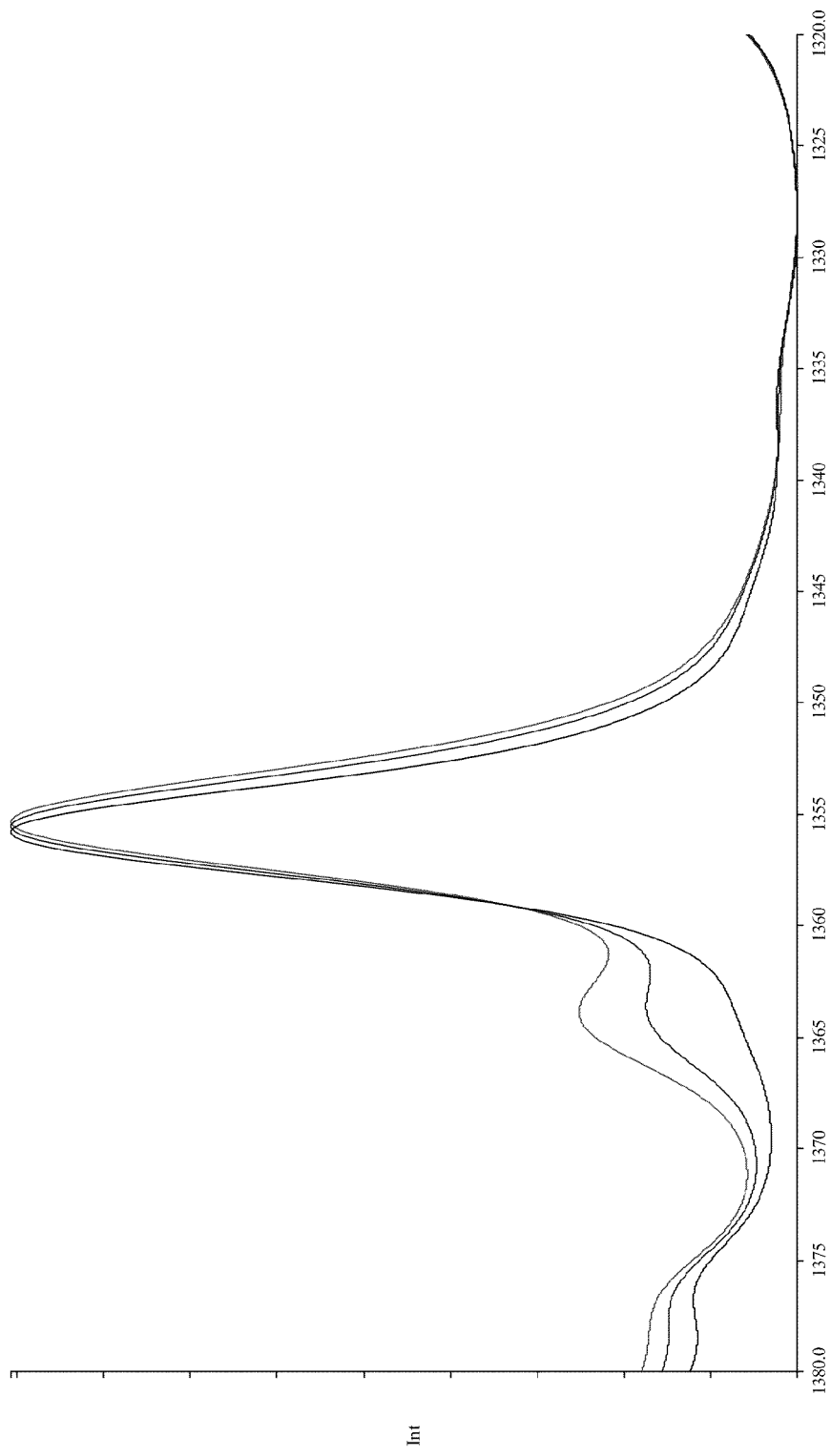
Figure 5. FT-Raman spectra of three omeprazole batches: 100 (A-form); 101 (a mixture of A and B forms); and 102 (B-form).

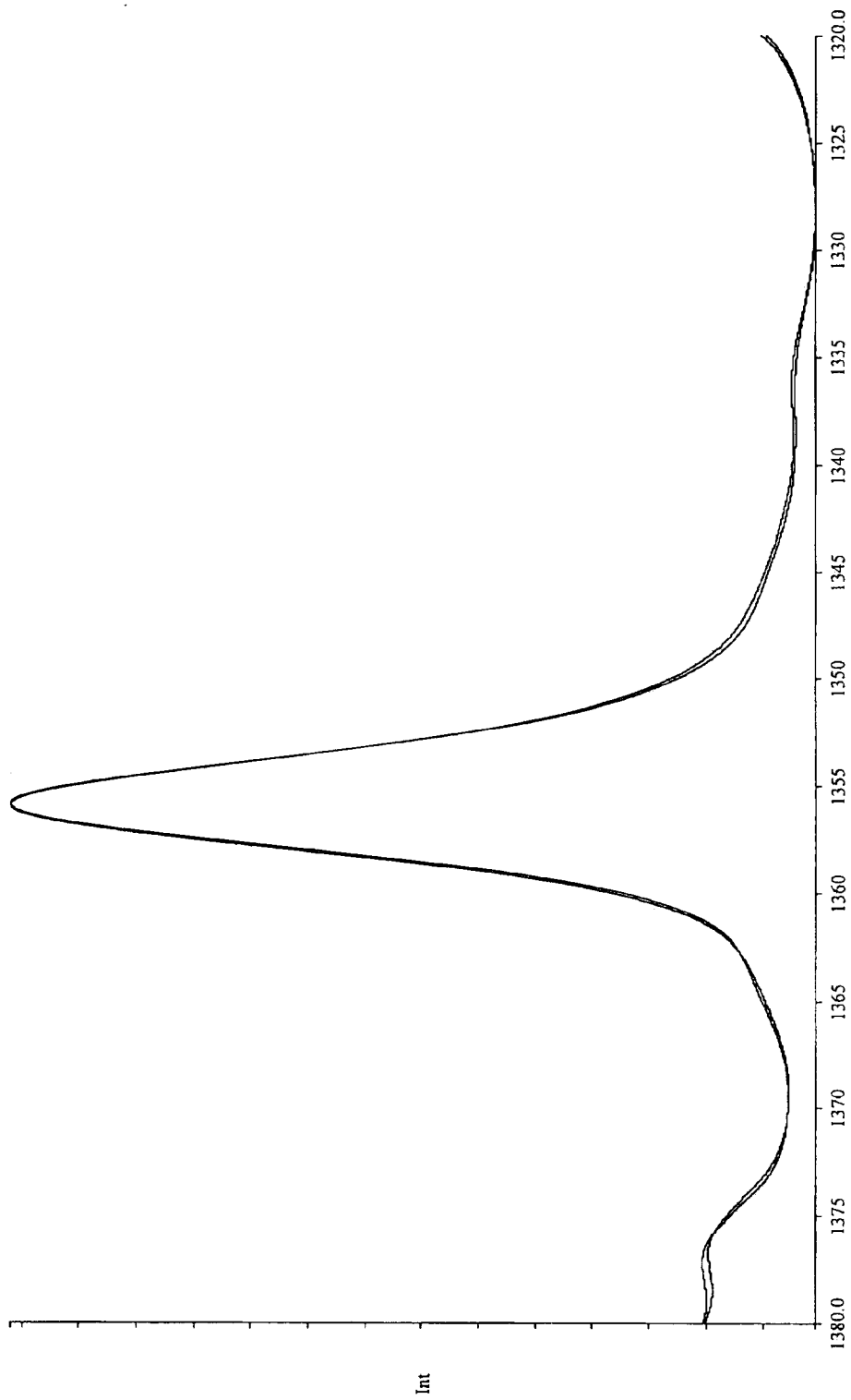
Figure 6. FT-Raman spectra of two different batches in the region 1380-1320 cm$^{-1}$.

RAMAN SPECTROSCOPIC METHOD FOR DETERMINING THE RATIO OF 5-METHOXY AND 6-METHOXY ISOMERS OF OMEPRAZOLE

This application is a continuation of U.S. patent application Ser. No. 11/284,434, filed 21 Nov. 2005 now abandoned, which is a continuation of U.S. patent application Ser. No. 10/284,828, filed 31 Oct. 2002, abandoned, which claims the benefit of provisional U.S. Patent Application Ser. No. 60/334,853, filed 31 Oct. 2001.

FIELD OF THE INVENTION

The present invention relates to a novel method to determine the ratio of 5-methoxy and 6-methoxy isomers of omeprazole present in a mixture thereof. The method uses different Raman scattering efficiency values for the 5-methoxy and 6-methoxy isomers.

BACKGROUND OF THE INVENTION AND PRIOR ART

Omeprazole is a proton pump inhibitor, i.e. effective in inhibiting gastric acid secretion, and is useful as an antiulcer agent In a more general sense, omeprazole may be used for treatment of gastric-acid related diseases in mammals and especially in man.

The compound 5-methoxy-2-[[(4-methoxy-3,5-dimethyl-2-pyridinyl)methyl]sulfinyl]-1H-benzimidazole, having the generic name omeprazole, as well as therapeutically acceptable is salts thereof, are described in EP 5129. Ohishi et al., Acta Cryst (1989), C45, 1921-1923, describe single crystal X-ray data and the derived molecular structure of one crystal form of omeprazole. A second crystal form of omeprazole is disclosed in WO 99/08500. These crystal forms are referred to herein as omeprazole forms B and A, respectively.

WO 01/14367 discloses isomers of omeprazole having the methoxy group on the benzimidazole ring at either the 6- or the 5-position. These two forms are referred to herein as "6-methoxy" and "5-methoxy", respectively or alternatively referred to as "6-isomer" and "5-isomer", respectively. WO 01/13919 discloses a method based on FT-Raman spectroscopy to determine the ratio of the 6- and 5-isomer of omeprazole present in a mixture thereof. The method of WO 01/13919 is based on the assumption that the 5-isomer and the 6-isomer have the same Raman scattering efficiency.

Isomers are chemical compounds that have the same molecular formulae but different molecular structures or different arrangements of atoms in space (see A Dictionary of Science, Oxford University Press, 1999). In structural isomerism the molecules have different molecular structures, i.e. they may be different types of compound or they may simply differ in the position of the functional groups in the molecule. Structural isomers generally have different physical and chemical properties. Tautomerism is a type of isomerism in which the two isomers (tautomers) are in equilibrium. The most wellknown tautomerism is the keto-enol tautomerism. In the keto-enol tautomerism one compound containing a —CH$_2$—CO— group (the keto form of the molecule) is in equilibrium with one containing the —CH=C(OH)— group (the enol). The keto-enol tautomerism occurs by migration of a hydrogen atom between a carbon atom and the oxygen on an adjacent carbon. Tautomers can therefore be said to be isomers that are rapidly interconverted in solution phase. The keto-enol tautomerism is schematically shown in Scheme 1 below.

Scheme 1 - The keto-enol tautomerism

keto          enol

Benzimidazole is also wellknown to exhibit tautomerism, see e.g. Lee and Jeoung, "Synthesis and Tautomerism of 2-Aryl- and 2-heteroaryl Derivatives of Benzimidazole", J. Heterocyclic Chem., 33, 1711 (1996); and Jacoby et al, "A comparison of intermolecular vibrations and tautomerism in benzimidazole, benzotriazole and their binary water clusters", Appl. Phys. B71, 643-639, (2000), and its 13C-NMR spectrum shows only four peaks in spite of seven carbon atoms being present. Structure, atom numbering, and tautomerism of benzimidazole are shown in Scheme 2 below.

Scheme 2 - Structure, atom numbering, and tautomerism of benzimidazole

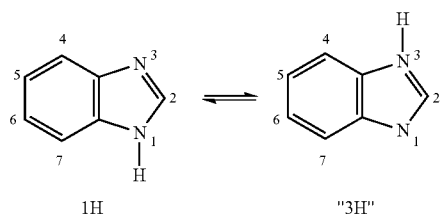

1H          "3H"

In the benzimidazole case the tautomerism occurs by migration of a hydrogen atom between the two nitrogen atoms. However, the 1H and "3H" tautomers are identical to each other unless the benzimidazole is assymetrically substituted. This phenomenon is discussed in U.S. Pat. No. 5,039,806 which relates to 2-pyridinyl methylsulfinyl benzimidazole compounds structurally related to omeprazole.

Scheme 3 - Structure, atom numbering and tautomerism of omeprazole

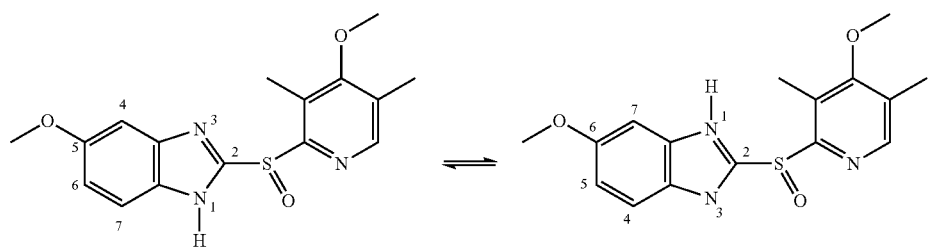

| Tautomer: | 1H | "3H" |
|---|---|---|
| IUPAC: | 5-methoxy-2-[[(4-methoxy-3,5-di methyl-2-pyridinyl)methyl]sulfinyl]-1H-benzimidazole | 6-methoxy-2-[[(4-methoxy-3,5-di methyl-2-pyridinyl)methyl]sulfinyl]-1H-benzimidazole |

Omeprazole with its methoxy group in the 5 position of the benzimidazole is monosubstituted and is thus assymetrically substituted. Consequently the 1H and "3H" tautomers are not identical. The IUPAC-nomenclature of these two isomers are 5-methoxy-2-[[(4-methoxy-3,5-dimethyl-2-pyridinyl)methyl]sulfinyl]-1H-benzimidazole and 6-methoxy-2-[[(4-methoxy-3,5-dimethyl-2-pyridinyl)methyl]sulfinyl]-1H-benzimidazole, referred to herein as the 5-methoxy and 6-metoxy isomers, as is indicated in Scheme 3 above.

The 5-isomer of omeprazole is thus a tautomer to the 6-isomer of omeprazole.

As discussed above tautomers are isomers that are rapidly interconverted in solution. This interconversion is very rapid but can be slowed down by decreasing the temperature. Two tautomers usually have different energy in solution and one tautomer (or isomer) is therefore of lower energy and more stable.

Solid phase is different from solution phase and the interconversion of tautomers (isomers) is usually non-existing in the solid phase. However, two tautomers may still be of different energy and one tautomer may therefore be more stable than the other also in the solid state.

Crystallisation is a process to precipitate a solid material from a solution thereof by allowing the concentration of the material to be above the saturation point so that the excess of the material is separated as crystals.

Polymorphism is the ability of elements or compounds to exist in more than one crystal is form, with each having the same chemical composition but different physical properties due to differences in the arrangement of atoms (A Dictionary of Earth Sciences, Oxford University Press 1999). Examples of polymorphs are graphite and diamond (both carbon); alpha and beta quartz (both $SiO_2$); and calcite (hexagonal) and aragonite (orthorhombic), both forms of $CaCO_3$. The external form of the crystal is referred to as the crystal habit. The atoms, ions, or molecules forming the crystal have a regular arrangement and this is the crystal structure (A Dictionary of Science, Oxford University Press, 1999).

Polymorphs differ in their crystal structures and they often have different properties, like rate of dissolution, stability and melting point. Different polymorphs can be characterized by e.g. X-ray Powder Diffraction (XRPD), differential scanning calorimetry (DSC), microscopy or spectroscopy. XRPD measurements show mainly variation in the unit cell parameters, while Raman spectroscopy mainly shows differences in molecular conformation. It is common in polymorphs that both the unit cell and the molecular conformation vary.

Omeprazole exists in two different crystal forms (polymorphs). The first is disclosed by Ohishi et al., Acta Cryst (1989), C45, 1921-1923, and is referred to as omeprazole form B. The second polymorph is disclosed in WO 99/08500 and is referred to as omeprazole form A. Omeprazole form A is in the solid state more stable than omeprazole form B, both thermodynamically and chemically. Omeprazole form B can be converted into form A by recrystallisation.

Omeprazole form A consists of the 6-isomer and omeprazole form B consists of a mixture of the 6- and 5-isomers, more specifically it consists of about 86% 6-isomer and about 14% 5-isomer (corrected values).

The different isomers and crystal forms of omeprazole can thus either be explained as a difference in the distribution of 5- and 6-methoxy isomer, or as a difference in the distribution between crystal forms A and B.

The amount of form A and form B is related to the amount of 5-isomer and 6-isomer, pure form A having no 5-isomer, pure form B having about 20% 5-isomer, and about 80% 6-isomer (FT-Raman values, not corrected for solid-state NMR data). The corresponding corrected values for form B is as discussed above about 86% 6-isomer and about 14% 5-isomer.

In the Raman spectrum of omeprazole, a peak is observed at 1355 $cm^{-1}$. If the 5-methoxy isomer is present, an additional Raman peak is observed at 1364 $cm^{-1}$ that is absent for the spectrum of pure 6-methoxy isomer. If the intensity of the two peaks is measured then the relative amount of 5- and 6-methoxy isomer present in a mixture thereof can be determined from the peak ratio.

However, it has now surprisingly been found that the two isomers of omeprazole have different Raman scattering efficiency and this has to be taken into account when calculating the amount of 5- and 6-isomer of omeprazole. If this is not properly done the wrong ratio of 5- and 6-isomer of omeprazole present in a mixture thereof will be calculated. This is of importance since mixtures, wherein the isomers have different ratios, have different solid state stability.

The FT-Raman spectrum is specific for omeprazole and differs from that of even closely related compounds, eg omeprazole salts. The band pair at 1355/1364 $cm^{-1}$ is characteristic for the 5- and 6-isomers of omeprazole.

BRIEF DESCRIPTION OF THE DRAWINGS

FIG. 1 shows the correlation of fraction of 5-isomer determined with FT-Raman and ssNMR analysis.

FIG. 2 is XRPDs of omeprazole form A and form B in the range 2θ8-30°, showing the different diffractograms. The peak at ca 25.5° is the internal reference, corundum.

FIG. 3 is XRPDs of three different batches of omeprazole. The three omeprazole batches 100 (form A), 101 (form A/B) and 102 (form B) are clearly different. It can be seen that batch 101 is intermediate between 100 and 102 at e.g. 2θ24° and 27.5°. The peak at ca 25.5° is the internal reference, corundum.

FIG. 4 is FT-Raman spectra of omeprazole forms A and B. All spectra were normalized to the band at around 1355 $cm^{-1}$. The intensity around 1365 $cm^{-1}$ is proportional to the relative amount of B-form and 5-isomer. From top to bottom at 1365 $cm^{-1}$, the curves represent: B-form and A-form.

FIG. 5 is FT-Raman spectra of the three omeprazole batches 100, 101, and 102. All spectra were normalized to the band at around 1355 $cm^{-1}$. The intensity around 1365 $cm^{-1}$ is proportional to the relative amount of 5-isomer. From top to bottom at 1365 $cm^{-1}$, the curves represent: Batches 102 (B-form), 101 (a mixture of A and B forms), 100 (A-form).

FIG. 6 is FT-Raman spectra of two different batches of omeprazole in the region 1380-1320 $cm^{-1}$.

DESCRIPTION OF THE INVENTION

It has surprisingly been found that the two isomers of omeprazole have different Raman scattering efficiency. It is thus an object of the present invention to provide a method determine the ratio of 5-methoxy and 6-methoxy isomers of omeprazole using different Raman scattering efficiency values for the 5-methoxy and 6-methoxy isomers. The present method using scaled Raman scattering efficiency values is advantageous since it gives the true amount of the 5-isomer and 6-isomer of omeprazole present in a mixture thereof.

Omeprazole form A is thermodynamically more stable than form B. It has additionally surprisingly been found that the amount of omeprazole form A present in a mixture of omeprazole form A and B is of importance for the stability of said mixture. The higher amount of omeprazole form A present in a mixture the more stable the mixture tends to be.

It is therefore of great importance to be able to adequately determine the ratio of 5-methoxy and 6-methoxy isomers of omeprazole in a mixture thereof.

The amount of 5- and 6-isomer was determined with FT-Raman spectroscopy and with solid-state NMR spectroscopy (ssNMR), and a correlation was calculated between the two methods, using linear regression. In the FT-Raman determination there is one unknown, since it is assumed that the 5-isomer and the 6-isomer have the same Raman scattering efficiency. With this assumption, the following data were obtained, as reported in Table 1.

TABLE 1

Determination of fraction of 5-isomer with FT-Raman and ssNMR analysis.

| Sample | Fraction 5-isomer ssNMR | Fraction 5-isomer FT-Raman |
|---|---|---|
| 1 | 0.0 | 0.0 |
| 2 | 0.05 | 0.07 |
| 3 | 0.11 | 0.18 |
| 4 | 0.14 | 0.20 |
| 5 | 0.14 | 0.20 |
| 6 | 0.28 | 0.44 |
| Intercept | | −0.0062 |
| Slope | | 1.5655 |
| Correlation coefficient | | 0.9972 |

The data are also illustrated in FIG. 1. Note that in FIG. 1 the point with abscissa 0.14 corresponds to two different batches.

Table 1 and FIG. 1 confirm that the determination of 5- and 6-isomer in omeprazole with ssNMR and FT-Raman spectroscopy have a high correlation. It was mentioned above that the FT-Raman determination has an unknown. The slope in the correlation is 1.5655, the reciprocal of which is 0.6388. Hence, a scaling factor of 0.64 must be used in the FT-Raman method to calculate the "true" percentage of 5-isomer. The "true" percentage is referred to as a "corrected" value. If the scaling factor of 0.64 is not used then the value is referred to as "uncorrected" or "not corrected".

| This leads to the following numbers: | |
|---|---|
| Intercept: | −0.0062 × 0.64 = −0.0040 |
| Slope: | 1.5655 × 0.64 = 1.00 |
| Correlation coefficient: | 0.9972 |

The relative amount of 5-isomer is determined by Raman spectroscopy from the following equation: Amount of 5-isomer=$I_{1364}(I_{1355}+I_{1364})\times 0.64$.

Thus, the 5-isomer has a higher Raman scattering efficiency than the 6-isomer.

For NMR spectroscopy, the signal from a carbon atom in a certain position is directly proportional to the concentration. Hence, no scattering efficiency is involved and no correction is necessary for ssNMR. Moreover, because of the closeness of the 1355 and 1364 cm$^{-1}$ Raman bands, the relative Raman scattering efficiency determined will be independent of the Raman instrument used.

XRPD can also be used to determine the relative amounts of 5- and 6-isomer in a mixture thereof. XRPD data confirms that the scaling factor between uncorrected and corrected values is 0.64.

Tests have been performed on omeprazole form A, form B and mixtures thereof with XRPD and FT-Raman spectroscopy. The XRPD measurements on the A and B forms indicate differences in the unit cell dimensions (FIG. 2) and the Raman measurements show differences in the 5/6-isomer ratio (FIG. 4).

As a comparison, testing has been done on batches 100, 101 and 102.

TABLE 2

The batches shown in the figures and the 5/6-isomer ratio determined by FT-Raman spectroscopy and the A/B ratio determined with XRPD.

| Batch | % 5-isomer (uncorrected values) [Raman spectroscopy] | Ratio A/B-form [XRPD] | % 5-isomer (corrected values) [Raman spectroscopy] |
|---|---|---|---|
| Form A | <2% | 100:0 | <2% |
| 100 | 2 | 99:1 | <2% |
| 101 | 12 | 54:46 | 8% |
| 102 | 18 | 22:78 | 12 % |
| Form B | 20 | 0:100 | 14 % |

Solid State NMR

The ratio of 5-methoxy and 6-methoxy isomers of omeprazole present in a mixture thereof can also be determined by Solid State NMR (ssNMR), e.g. using cross polarization magic angle spinning (CP-MAS) technique.

In order to arrive at a complete assignment, a specifically $^{13}$C-labelled sample was synthesized which gives a hundred-fold NMR-intensity increase for the seven enriched carbon atoms of the benzimidazole group. The spectrum for $^{13}$C-labelled omeprazole was assigned with a 2D RFDR experiment and clearly shows two similar but separate correlation networks attributed to the 5- and 6-methoxy isomers. The chemical shift differences caused by the tautomerism are of similar magnitude as those obtained from solution NMR experiments. The combined data result in unambigous assignments for every carbon atom of omeprazole, though there are some overlapping signals. Spectral regions containing non-overlapping signals from the 5- and 6-methoxy isomers can be used for quantification also for natural abundance omeprazole samples.

The ratio of 5-methoxy and 6-methoxy isomers of omeprazole present in a mixture thereof can also be determined by X-ray powder diffraction.

Specificity

The FT-Raman spectrum is specific for omeprazole and differs from that of even closely related compounds, eg omeprazole salts. The band pair at 1355/1364 cm$^{-1}$ thus characteristic for the 5- and 6-isomers.

Precision

Repeatability of Analysis

Repeatability was done for batch ASP 255. Three operators analyzed the batch and evaluated the data. For every spectrum, a new sampling was made from the same jar. The results are reported in Table 3, where average, standard deviation, and relative standard is deviation are shown. Thus, repeatability was found to be high. The data in Table 3 are reported without correction factor.

TABLE 3

Determination of fraction of 5- and 6-isomer with
FT-Raman spectroscopy, for omeprazole batch
ASP 255 (without correction factor).

| | $I_{1364}/$ $(I_{1355} + I_{1364})$ Operator 1[a] | $I_{1364}/$ $(I_{1355} + I_{1364})$ Operator 2 | $I_{1364}/$ $(I_{1355} + I_{1364})$ Operator 3 |
|---|---|---|---|
| 1 | 0.115 (0.112) | 0.112 | 0.112 |
| 2 | 0.118 (0.114) | 0.112 | 0.115 |
| 3 | 0.115 (0.112) | 0.112 | 0.115 |
| 4 | 0.118 (0.113) | 0.112 | 0.115 |
| 5 | 0.118 (0.113) | 0.112 | 0.115 |
| 6 | 0.118 (0.114) | 0.110 | 0.115 |
| 7 | 0.115 | | |
| 8 | 0.115 | | |
| 9 | 0.115 | | |
| 10 | 0.112 | | |
| N | 6 | 6 | 10 |
| Average | 0.117 | 0.112 | 0.114 |
| Standard deviation | 0.0015 | 0.0008 | 0.0013 |
| Relative S. Dev. | 1.3% | 0.7% | 1.1% |

[a]Values in parenthesis determined with computer software.

Intermediate Precision

Intermediate precision can be evaluated from the averages in Table 3. Moreover, intermediate precision was determined from measurement on 10 different batches which were analyzed on the same instrument, by the three different operators, on different days, with new sampling for every spectrum. These measurements are reported in Table 4.

TABLE 4

Determination of fraction of 5- and 6-isomer with FT-Raman
spectroscopy, for 10 batches of omeprazole (n = 1).

| Batch AAAAE-156- | $I_{1364}/$ $(I_{1355} + I_{1364})$ Operator 1 | $I_{1364}/$ $(I_{1355} + I_{1364})$ Operator 2 | $I_{1364}/$ $(I_{1355} + I_{1364})$ Operator 3 | Average | Standard deviation |
|---|---|---|---|---|---|
| 7A | 0.451 | 0.444 | 0.446 | 0.447 | 0.004 |
| 8A | 0.141 | 0.139 | 0.137 | 0.139 | 0.002 |
| 29G | 0.099 | 0.090 | 0.095 | 0.095 | 0.005 |
| 29H | 0.093 | 0.087 | 0.087 | 0.089 | 0.003 |
| 24H | 0.082 | 0.084 | 0.084 | 0.083 | 0.001 |
| 11219910042 | 0.076 | 0.071 | 0.073 | 0.073 | 0.003 |
| 15B | 0.070 | 0.071 | 0.068 | 0.070 | 0.002 |
| 32N | 0.070 | 0.065 | 0.065 | 0.067 | 0.003 |
| 23F | 0.033 | 0.037 | 0.031 | 0.034 | 0.003 |
| 32D | 0.020 | 0.019 | 0.019 | 0.019 | 0.001 |

The 10 batches gave average values in the range 0.019-0.447, with standard deviation in the range 0.001-0.005. Relative standard deviation was in the range 0.9-8.8%, naturally with higher RSD for low fraction of 5-isomer.

For all the measurements reported in Tables 3-4, $I_{1364}$ and $I_{1355}$ were evaluated graphically to from printed figures. For measurements number 1-6 by operator 1 in Table 3, computer software was used to determine $I_{1364}$ and $I_{1355}$, with subtraction of the baseline around 1328 cm$^{-1}$, $I_{1328}$. Whereas the graphical evaluation in Table 3 gave values of 0.115-0.118, the computer evaluation gave values of 0.112-0.114. This deviation is similar to the difference between different operators using graphical evaluation (see Table 3).

Quantitation Limit

In Table 4, the sample with 1.9% 5-isomer was determined by the three operators with a standard deviation of 0.1%. Hence, the quantitation limit can be set as 2% 5-isomer, uncorrected value, which corresponds to 1,3% 5-isomer, corrected value.

Detection Limit

Detection limit is illustrated in FIG. 6.

In FIG. 6, one curve is representative for the pure 6-isomer, while the other curve belongs to batch 100, determined to contain 1.4% 5-isomer, 98.6% 6-isomer (corrected values). Close inspection of the curves, in particular around 1364 cm$^{-1}$, indicates that the difference between the two curves can be distinguished, but also that this difference is close to the limit of detection. However, the limit of quantitation was determined above as 1.3% 5-isomer so it is reasonable to set the limit of detection as <1.3% 5-isomer as well.

Accuracy

The present method is seen from Tables 1 and 2 and FIG. 1 to yield an accurate determination of the amount of 5- and 6-isomer present in a sample of omeprazole.

The method of the present invention can be used to determine the ratio of 5-methoxy and 6-methoxy isomers of omeprazole present in a mixture thereof in bulk form as well as in admixture with pharmaceutical excipients, e.g. conventional pellets.

EXAMPLES

| Equipment An example of instrument and settings is given below: | |
|---|---|
| Instrument: | Perkin-Elmer System 2000 NIR FT-Raman |
| Detector: | InGaAs |
| Beam splitter: | quartz |
| B-stop: | 21.2 mm |
| J-stop: | 6.47 mm, corresponding to 4 cm$^{-1}$ at 15000 cm$^{-1}$ |
| Resolution: | 2 cm$^{-1}$ |
| Apodization: | filler |
| Gain: | 1 |
| OPD velocity: | 0.1 cm/sec |
| Interferogram type: | bi-directional, double-sided |
| Phase correction: | magnitude |
| Data range: | 0-4000 cm$^{-1}$ |
| Data interval: | 0.5 cm$^{-1}$ |
| Laser power: | 500 mW at sample |
| Number of scans: | 128 |

Example 1

Place omeprazole substance or powder in a suitable holder, then place the holder in the FT-Raman instrument. Preferably, place the compound in a suitable glass container, eg ca 30 mg of compound in an NMR tube with 5 mm outer diameter, tap the sample to pack it, then place the tube in the FT-Raman instrument in a holder that is able to rotate the sample.

Record the FT-Raman spectrum between 0 and 4000 cm$^{-1}$.

Also record the FT-Raman spectrum of a reference sample that is pure 6-isomer. Alternatively, retrieve such spectrum from a library.

Display the spectrum obtained together with the spectrum of pure 6-isomer in the region 1380-1320 cm$^{-1}$, and normalize on the 1355 cm$^{-1}$ peak (on Perkin-Elmer 2000 use: "autoscale y"). Measure the intensity $I_{1355}$ at 1355 cm$^{-1}$, with subtraction of the background around 1328 cm$^{-1}$. Measure the intensity $I_{1364}$ at 1364 cm$^{-1}$, with subtraction of the background obtained from the normalized spectrum of the pure 6-isomer.

The relative amount of 5-isomer is determined by Raman spectroscopy from the following equation:

$$\text{Amount of 5-isomer} = I_{1364}/(I_{1355}+I_{1364}) \times 0.64.$$

The invention claimed is:

1. In a Raman spectrographic method for determining the ratio of 5-methoxy and 6-methoxy isomers of an omeprazole compound comprising one or both isomers by measuring the intensities of peaks at 1364 cm$^{-1}$ and 1355 cm$^{-1}$ of the 5-methoxy and 6-methoxy isomers, respectively the improvement comprising:

measuring the amount of each isomer in the omeprazole compound by conducting Raman spectroscopy using different Raman scattering efficiency values for the 5-methoxy and 6-methoxy isomers with the scaling factor 0.64.

2. The method according to claim 1, wherein the 5-methoxy isomer has a higher Raman scattering efficiency than the 6-methoxy isomer.

3. The method according to claim 1, wherein the mixture of 5- and 6-isomers is a bulk form.

4. The method according to claim 1, wherein the mixture of 5- and 6-isomer is present in a pharmaceutical formulation containing additional pharmaceutical excipients.

* * * * *